(12) United States Patent
Mil et al.

(10) Patent No.: US 11,523,962 B2
(45) Date of Patent: Dec. 13, 2022

(54) POSITIONABLE FOOT PORTION OF A MEDICAL DEVICE

(71) Applicant: Borcad Medical A.S., Frycovice (CZ)

(72) Inventors: Petr Mil, Baska (CZ); Tomas Chlopcik, Bohuslavice (CZ)

(73) Assignee: Borcad Medical A.S., Frycovice (CZ)

( * ) Notice: Subject to any disclaimer, the term of this patent is extended or adjusted under 35 U.S.C. 154(b) by 115 days.

(21) Appl. No.: 16/333,035

(22) PCT Filed: Sep. 13, 2017

(86) PCT No.: PCT/CZ2017/050041
§ 371 (c)(1),
(2) Date: Mar. 13, 2019

(87) PCT Pub. No.: WO2018/054400
PCT Pub. Date: Mar. 29, 2018

(65) Prior Publication Data
US 2019/0247260 A1 Aug. 15, 2019

(30) Foreign Application Priority Data

Sep. 20, 2016 (CZ) .............................. CZ2016-584

(51) Int. Cl.
*A61G 13/12* (2006.01)
*A61G 13/00* (2006.01)
(Continued)

(52) U.S. Cl.
CPC ....... *A61G 13/125* (2013.01); *A61G 13/0009* (2013.01); *A61G 13/08* (2013.01);
(Continued)

(58) Field of Classification Search
CPC .. A61G 13/125; A61G 13/0009; A61G 13/08; A61G 13/1245; A61B 2090/506; B25J 3/02; B43L 13/00
(Continued)

(56) References Cited

U.S. PATENT DOCUMENTS 218,210 A * 8/1879 Alling et al. .......... B60N 2/502
 248/585
3,417,953 A * 12/1968 Paula ................. F16M 11/2014
 248/284.1
(Continued)

FOREIGN PATENT DOCUMENTS

EP 1813243 A2 8/2007
WO 93/09750 A1 5/1993

OTHER PUBLICATIONS

WIPO, International Search Report, dated Jan. 4, 2018, in International Application No. PCT/CZ2017/050041, filed Sep. 13, 2017.
(Continued)

*Primary Examiner* — Myles A Throop
(74) *Attorney, Agent, or Firm* — Thedford I. Hitaffer; Hitaffer & Hitaffer, PLLC

(57) ABSTRACT

The object of the invention is a foot portion (2a) of a medical device, such as gynecological examination bed or a birthing bed. The aim of the invention is to provide a method for moving the foot portion into the required position quickly, effectively and not limiting the actions of medical personnel. An advantage of the present invention is moving the foot portion under the rest area (1) without undesirable protrusion. Movement of the foot portion (2a) under the rest area (1) is performed around a column (5), which is attached under the side edge of a seating portion (3). Such arrangement of the column leaves free space under the rest area (1) for moving the foot portion (2a). Movement of the foot portion (2a) is performed with minimum protrusion over the
(Continued)

borderline of the rest area (1) by means of a parallelogram. The foot portion according to the present invention may be also positioned horizontally and vertically, according to the patient's need during the procedure. For each movement, there are available separate moving mechanisms and latching mechanisms.

20 Claims, 7 Drawing Sheets

(51) Int. Cl.
*A61G 13/08* (2006.01)
*A61B 90/50* (2016.01)
*B43L 13/00* (2006.01)
*B25J 3/02* (2006.01)

(52) U.S. Cl.
CPC .... *A61G 13/1245* (2013.01); *A61B 2090/506* (2016.02); *B25J 3/02* (2013.01); *B43L 13/00* (2013.01)

(58) Field of Classification Search
USPC .............................................................. 5/624
See application file for complete search history.

(56) References Cited

U.S. PATENT DOCUMENTS

| | | | | |
|---|---|---|---|---|
| 3,866,251 A * | 2/1975 | Pounds | ................ | A47C 20/022 5/624 |
| 4,206,525 A * | 6/1980 | Williams | ............... | A47C 21/00 5/430 |
| 4,394,075 A * | 7/1983 | Brown | ............... | F16M 11/2014 224/185 |
| 4,454,781 A * | 6/1984 | Orii | ..................... | B21D 43/105 74/99 R |
| 4,581,778 A * | 4/1986 | Pontoppidan | ........ | A61G 7/1007 297/DIG. 10 |
| 4,724,555 A * | 2/1988 | Poehner | ................... | A61G 7/05 5/624 |
| 4,894,876 A * | 1/1990 | Fenwick | ............ | A61G 13/0009 5/602 |
| 4,985,946 A * | 1/1991 | Foster | .................... | A61G 7/00 5/430 |
| 5,054,141 A * | 10/1991 | Foster | ................... | A61G 7/0514 5/611 |
| 5,157,800 A | 10/1992 | Borders | | |
| 5,178,025 A * | 1/1993 | Bennett | .................... | A61G 5/14 74/105 |
| 5,226,187 A * | 7/1993 | Borders | ............. | A61G 13/0009 5/624 |
| 5,715,548 A * | 2/1998 | Weismiller | ............. | A61G 7/052 5/624 |
| 5,826,286 A * | 10/1998 | Cranston | .................. | A61D 3/00 5/942 |
| 5,941,175 A * | 8/1999 | Bannister | ............ | A61G 13/1245 108/20 |
| 6,226,821 B1 * | 5/2001 | Heimbrock | .......... | A61G 7/0507 5/602 |
| 6,408,464 B1 * | 6/2002 | Weismiller | ......... | A61G 13/0009 5/624 |
| 6,662,392 B2 * | 12/2003 | Heimbrock | .......... | A61G 1/0268 5/624 |
| 7,685,659 B2 * | 3/2010 | Heimbrock | ........ | A61G 13/0009 5/624 |
| 7,823,843 B2 * | 11/2010 | Oberlaender | .......... | F16M 11/18 248/278.1 |
| 7,992,832 B2 * | 8/2011 | Zhang | ................ | F16M 11/2092 248/585 |
| 9,119,753 B2 * | 9/2015 | Poulos | ................. | A61G 7/0509 |
| 9,204,730 B2 * | 12/2015 | Brown | .................... | A61G 5/125 |
| 9,810,371 B2 * | 11/2017 | Nakamura | ........... | F16M 13/022 |
| 10,179,077 B2 * | 1/2019 | Poulos | ................. | A61G 7/0506 |
| 10,835,430 B2 * | 11/2020 | Sweeney | ................. | A61G 7/16 |
| 2002/0108874 A1 * | 8/2002 | Metelski | ................ | A61B 90/25 206/316.1 |
| 2002/0178502 A1 * | 12/2002 | Beasley | ................. | A61G 7/015 5/618 |
| 2003/0088917 A1 * | 5/2003 | Ruehl | ................ | A61G 13/0009 5/624 |
| 2005/0102755 A1 * | 5/2005 | Jacobs | ................... | A61G 15/00 5/624 |
| 2007/0080275 A1 * | 4/2007 | Stachowski | ........ | F16M 11/2014 248/323 |
| 2007/0174964 A1 * | 8/2007 | Lemire | ................ | A61G 7/0506 5/600 |
| 2008/0067302 A1 * | 3/2008 | Olivera | .................. | F16M 11/08 248/183.1 |
| 2009/0031498 A1 * | 2/2009 | Girard | .................... | A61G 7/015 5/617 |
| 2010/0185211 A1 * | 7/2010 | Herman | ................. | A61B 90/50 606/130 |
| 2010/0223727 A1 * | 9/2010 | Newkirk | ............... | A61G 7/0755 5/602 |
| 2010/0242176 A1 * | 9/2010 | Newkirk | ............... | A61G 7/0524 5/602 |
| 2012/0198628 A1 * | 8/2012 | Richards | ................ | A61G 7/053 5/618 |
| 2013/0074637 A1 * | 3/2013 | Choi | ..................... | A61B 34/30 901/28 |
| 2017/0000676 A1 * | 1/2017 | Revenus | ................. | A61G 13/06 |
| 2017/0314731 A1 * | 11/2017 | Glaser | .................. | A61G 12/005 |
| 2019/0247252 A1 * | 8/2019 | Mil | ......................... | A61G 13/06 |
| 2020/0191322 A1 * | 6/2020 | Honaryar | ................ | F16H 21/44 |

OTHER PUBLICATIONS

WIPO, Written Opinion, dated Jan. 4, 2018, in International Application No. PCT/CZ2017/050041, filed Sep. 13, 2017.

* cited by examiner

POSITIONABLE FOOT PORTION OF A MEDICAL DEVICE

This application, filed under 35 USC 371, is a United States National Stage Application of International Application No. PCT/CZ2017/050041, filed Sep. 13, 2017, which claims priority to CZ Application No. PV 2016-584, filed on Sep. 20, 2016, the disclosures of which are incorporated herein by reference.

FIELD OF THE INVENTION

The technical solution is related to medical devices, such as beds and chairs used in obstetrics, surgery, oncology, gynecology, dialysis and further, for example, hospital beds, transport beds or operating tables, using a telescopic support column allowing change of the height position of the device.

BACKGROUND OF THE INVENTION

According to the present state of the art, the foot portion is attached to the structure of medical beds in movable manner in order to optionally adjust the position of the foot portion in relation to the rest part. The foot portion may be detachable from the medical bed, thus enlarging the operating space (area serving for medical personnel to perform the medical act, not being constrained by the medical bed or any of its parts) or it may be its integral part. In some embodiments, it is possible to remove the fixedly attached foot portions from the foot area by moving them out of the operating space, achieving the same effect as in case of detaching them. In present, several mechanisms for solution of the positionable foot portion of a medical bed are used. As the bed has several fields of utilization, the position of a patient depends on the type of medical procedure which is being performed as well as suitability of the position in relation to patient's health. By detaching or pulling the foot portion away, better access to the patient is allowed to the medical personnel.

The patent document CN101773439 describes a mechanism moving the foot portion by means of a scissor lift. The foot portion may be detached from the medical bed by unlocking the mechanical lock and detaching the portion from the bed structure. This solution requires intervention of medical personnel as well as space for storing the foot portion, which interferes with the course of the medical procedure.

The patent document U.S. Pat. No. 6,725,479 describes a mechanism of the foot portion attachable to the medical bed by means of extendable frame parts. The foot portion of this mechanism is mechanically detachable from the bed structure. This solution requires intervention of medical personnel as well as space for storing the foot portion, which interferes with the course of the medical procedure.

The patent document EP1028685 describes mechanism of foot portion structure, consisting of several parts which are independently movable in terms of vertical and horizontal position. The particular parts are covered with detachable layers of soft material. The foot portion structure is not detachable from the bed. This limits the range of utilization of the medical bed.

The patent document EP1813243 describes mechanism for vertical movement of the foot portion by means of sliding device. In the bottom position, it is possible to rotate the foot portion around a column and place it under the rest area. The column may be arranged only in the center of the bed, because of bi-directional rotation of the foot portion. Rotation causes protrusion into the operating space.

In the present state of the art, there are no available solutions for foot portion of medical beds, which would allow moving the foot portion under the bed without the limiting protrusion into the operating space.

SUMMARY OF THE INVENTION

The above-mentioned drawbacks are to a certain extent eliminated by a foot portion according to the present invention. The aim of the invention is to provide a method for moving the foot portion into the required position quickly, effectively and without limiting the actions of medical personnel. An advantage of the present invention is moving the foot portion under the rest area without undesirable protrusion.

This is realized by means of a horizontal movement mechanism, consisting of one or more movable arms or a translational guide or a parallelogram. Movement of the foot portion under the rest area is performed around a column, which is attached under the side border of the seating area, wherein the column is arranged with at least 70% of its plan view behind the longitudinal axis of the rest area, which lies in a direction longitudinal with the longer border of the rest area. This arrangement of the column leaves free space under the rest area and allows moving the foot portion without any undesirable protrusion.

Horizontal movement by means of parallelogram comprises two arms of the horizontal parallelogram, wherein these arms are rotationally attached to the column on one side or to a part of the rest area fixedly coupled with the column. On the other side, the arms are rotationally attached to the vertical movement mechanism. The horizontal parallelogram comprises also a latching mechanism of the horizontal movement of the foot portion. The overall protrusion of the foot portion over the borderline of the rest area of a medical device reaches the maximum of 70 mm during movement.

It is possible to change the position of the foot portion according to the present invention also vertically. Vertical movement mechanism of the foot portion is a parallelogram or a scissor mechanism. Vertical movement by means of a parallelogram comprises two arms of the vertical parallelogram. These arms are rotationally attached to the foot portion on one side and to the horizontal movement mechanism on the other side. The vertical movement mechanism further comprises a lockable spring rotationally coupled to the foot portion on one end and to the horizontal movement mechanism on the other end.

The foot portion is rotationally connected with the vertical movement mechanism, wherein the connection is provided in the center of the foot portion or on the border of the foot portion. The foot portion further comprises a lockable spring of the latching of tilting, wherein the spring is rotationally attached to the structure of the vertical movement mechanism on one side and it is rotationally attached to the foot portion on the other side, in the area distant from the rotational connection of the foot portion and the vertical movement mechanism of the foot portion.

All the movement mechanisms further comprise controllers arranged on pins under the foot portion, wherein these controllers are connected with the lockable latching springs by means of a Bowden cable. The lockable spring is a gas or mechanical lockable spring, or a linear drive with an electric motor. These springs make the movement of the foot part easier for medical personnel, while keeping it in the required position.

EXEMPLARY EMBODIMENTS OF THE INVENTION

Figure 1:
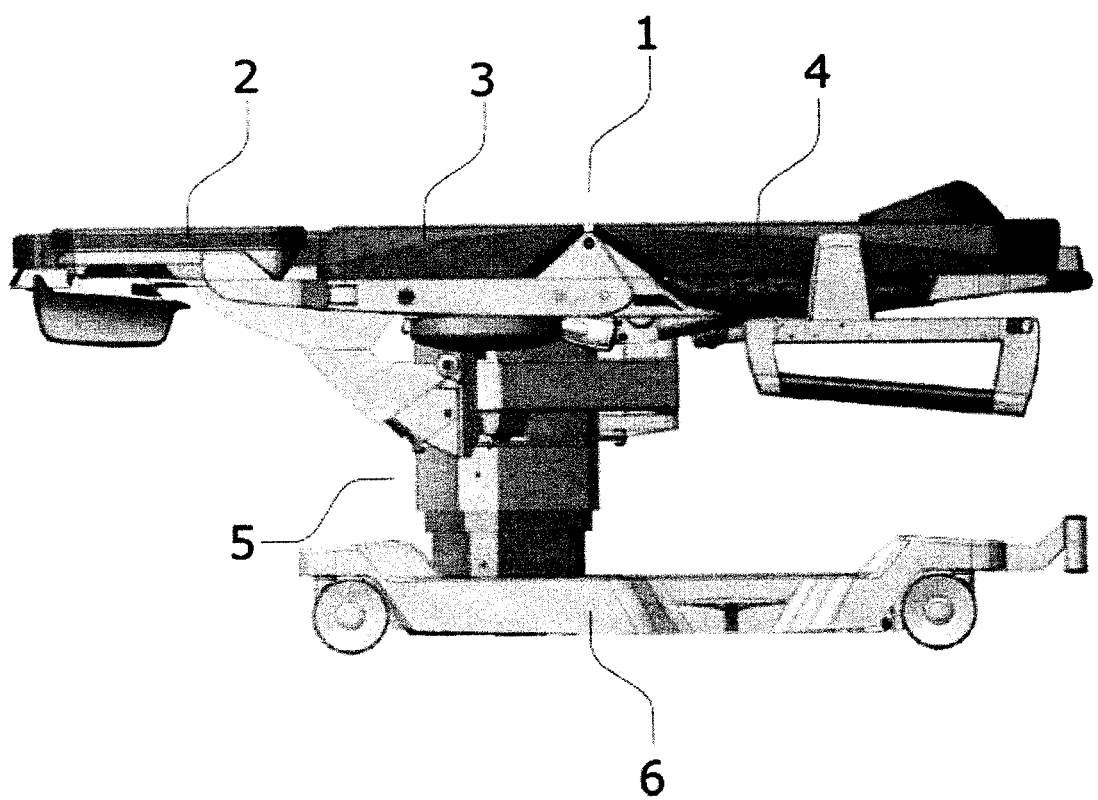
FIG. 1—a view on the medical device with the rest area of all parts in the same plane.

An exemplary embodiment of the invention is a medical device for, e.g. gynecological examination bed or a birthing bed, as it is illustrated in the FIG. 1. A part of the medical device is an upper rest area, which is arranged e.g. on a column 5 or a scissor lift, provided on a chassis 6. A column drive may consist of one or more telescopic segments.

The column 5 may consist of more concentric segments, where each of them, except the column arranged nearest to the chassis frame, comprise a motor intended for driving a particular segment.

Part of the upper support area is a detachable rest area 1. The rest area 1 is adapted for easy maintenance. The rest area 1 may be, for example, a layer of soft material for interaction with the patient's body. The rest area may consist of, for example, foamed polyurethane, cold foam or a combination thereof. The foam layer may be provided in a washable shell.

The chassis frame comprises wheels. At least three wheels, preferably four, and for improving the manipulation even a fifth central wheel may be added. Part of the wheels may be a brake system, which may be electrically, mechanically or hydraulically operated. Activation of the brake system may be performed by means of a manual controller, foot controller or automatically after a certain time period, during which the medical device is not moved, or a combination thereof.

An infusion stand holder may be rotationally arranged on the chassis frame. The infusion stand holder may be rotatably between the inactive and active position. In the active position, it is possible to insert an infusion stand into the infusion stand holder. In the inactive position, the infusion stand holder does not protrude outside the frame chassis, thus eliminating the risk of tripping.

The upper support area may consist of, for example, back portion 4, seating portion 3 and a foot segment 2. These portions may consist of, for example, two or more moldings and the top and bottom surface. The top and bottom surface may be a shaped sheet metal. The moldings may be mutually connected by means of, for example, welding, screwing, riveting or gluing, in order to form a central part. The central part is connected with the top or bottom surface by means of, for example, welding, screwing, riveting or gluing. After connecting the top and bottom surface a portion with enclosed area is formed. Enclosing the part creates a space suitable for, e.g. wiring, and the surface of the part can be maintained more easily.

Figure 2:
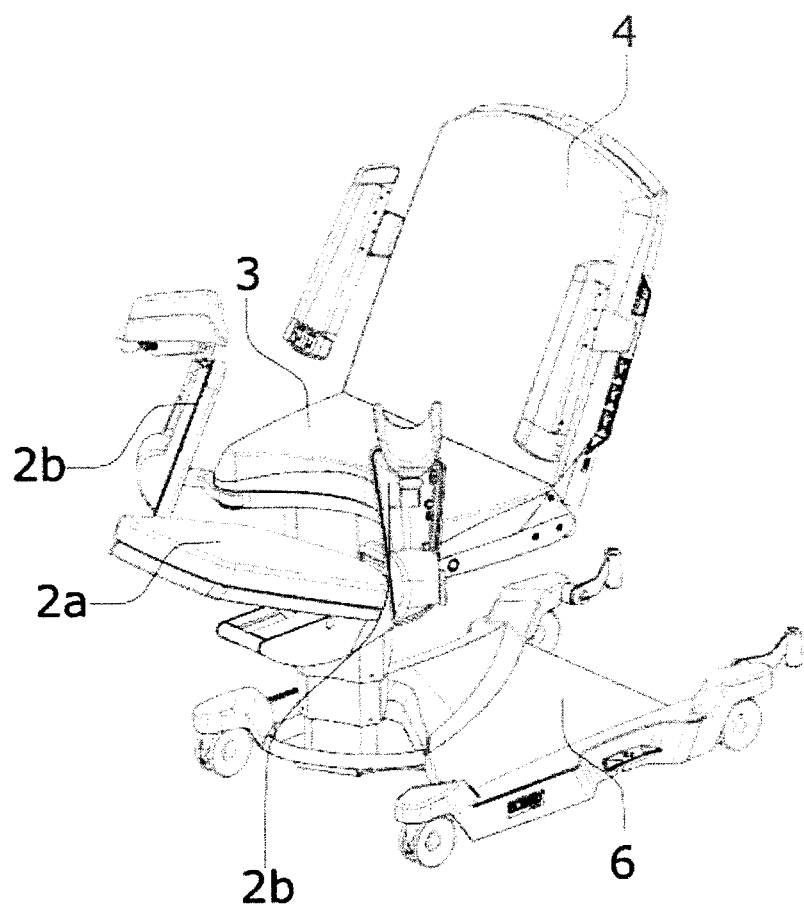
FIG. 2—a view on the medical device with a tilted back portion and a foot portion in the active position, lowered under the rest area.
Figure 3:
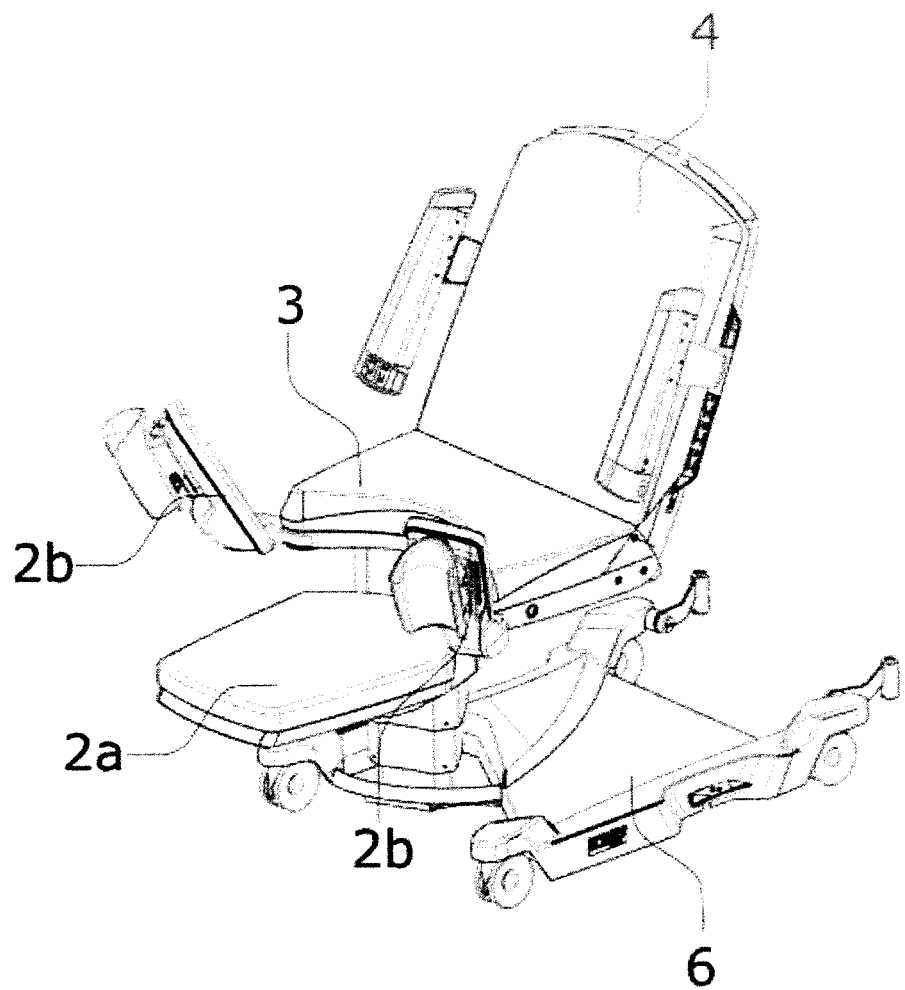
FIG. 3—a view on the medical device with a tilted back portion and a tilted foot portion in the active position, lowered under the rest area.
Figure 4:
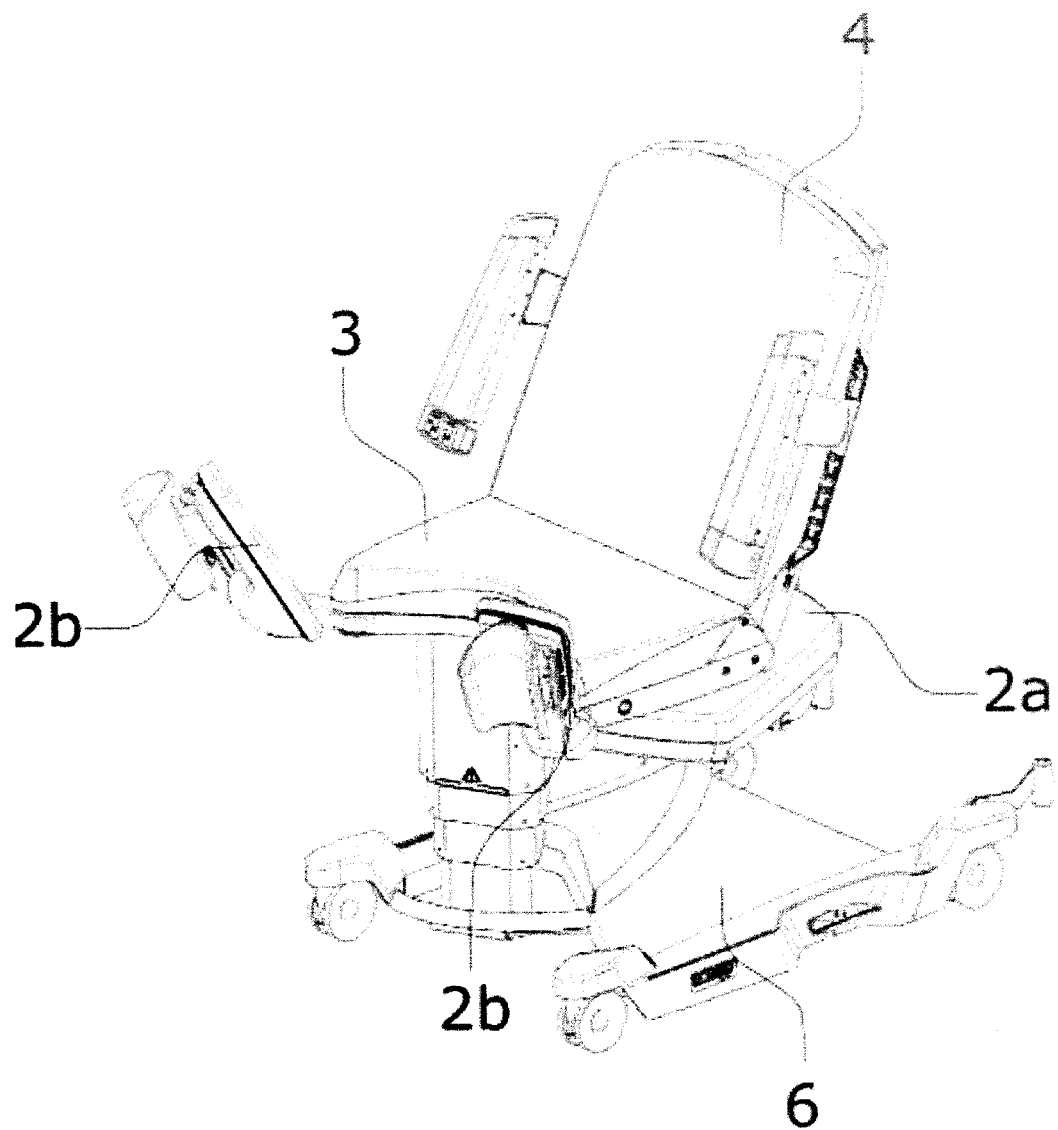
FIG. 4—a view on the medical device with a tilted back portion and a foot portion in the inactive position behind the column.

The foot segment 2 is further divided into foot supports 2b and the foot portion 2a, as it is illustrated in the FIGS. 2, 3 and 4. Together they form a segment with an enclosed surface. The foot supports 2b can be tilted. The foot support 2a may be used in the active position in various heights and various degrees of tilting. The term "active position" refers to the position, when the foot portion 2a is not in the inactive position. It is a position in which the foot portion is used as a part of the rest area 1 or eventually it is moved into a lower position than the level of the rest of the rest area, or it is tilted, serving as a support for patient's feet. The inactive position is the position of the foot portion after being moved around the column 5 under the rest area 1, where it is possible to move the foot portion in this exemplary embodiment after being lowered from the upper vertical position.

Movement of the foot portion 2a is provided by three independent mechanisms, which are mechanically controllable. Unlocking of the movement may be performed by means of a control latching element provided on the foot portion 2a. The latching element may be a system of one or more controllers locking and unlocking the possibility of movement in a certain direction, rods, springs and lock elements. For all independent movements, such as horizontal movement between the active and the inactive position, vertical movement within the active position and tilting, there are available separate lever controllers of unlocking and locking in this exemplary embodiment. Movement of the foot portion 2a from the active to the inactive position is performed in the horizontal plane. Movement of the foot portion 2a from the position, in which it is in the level of the seating portion, into the lower portion is performed in the vertical direction. After unlocking by means of the controller, it is possible to move the foot portion 2a within the range of the unlocked movement in the required direction. After unlocking in the active position, it is possible to move the foot portion 2a vertically as needed as well as optionally tilt it around the horizontal axis. The foot part 2a may be moved from the active position to the inactive position by means of moving it around the column 5 under the rest area 1 and this is possible whenever the foot part 2a is not in its highest position, i.e. it is under the level of the rest area 1, and movement to the inactive position therefore does not collide with the rest area 1.

The foot part 2a is attached to the upper segment of the column 5 by means of the horizontal and vertical movement mechanisms, which follow each other. Alternatively, it is possible to attach the foot portion 2a to the rest area 1. The horizontal movement mechanism is arranged closest to the column 5, the mechanism moving the foot portion between the active and the inactive position. Horizontal movement mechanism is followed by the vertical movement mechanism to which the foot portion 2a is rotationally connected, wherein the connection provides tilting of the foot portion 2a against the vertical movement mechanism. Alternatively, it is possible to attach the foot portion 2a to the vertical movement mechanism in a fixed manner.

Figure 5:
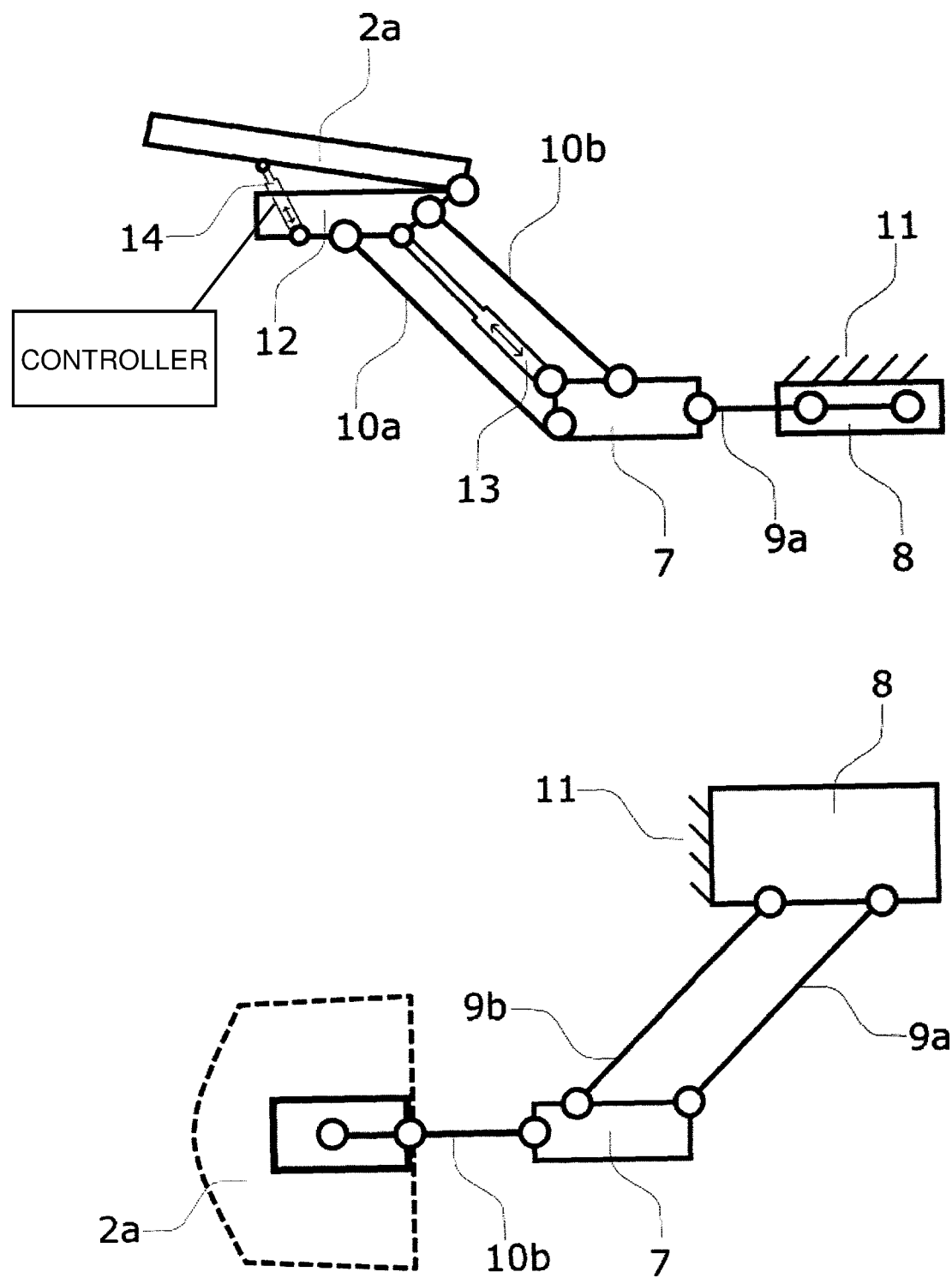
FIG. 5—schematic illustration of the structure of the positioning mechanisms of the foot portion with the parallelogram for vertical as well as horizontal movement and with a tilted rest area of the foot portion, in a side view and a top view.

The first exemplary embodiment of the movement mechanism is illustrated in the FIG. 5. Movement of the foot portion 2a from the active position to the inactive position under the rest area in this exemplary embodiment is provided by means of a parallelogram, which comprises four articulated joints connection via arms, wherein the opposite arms of the parallelogram are of the same length. Movement of the foot portion is rotational. Movement from the inactive position under the rest area in this exemplary embodiment is realized around the column 5, which is arranged under the side border of the rest area of the seating portion 3. The angle of movement of the mechanism is in the range of 0°-124° and in specific embodiments it depends on the position of the column 5 in structure of the medical bed. First two articulated joints of the parallelogram are attached to the fixed part 11 of the medical device, which is a column 5 or alternatively the upper frame or the connecting part 8 of the horizontal movement, wherein the fixed part 11 of the medical device at the same time represents an arm of the parallelogram. Other two articulated joints are attached to the connecting part 7 of the vertical movement, wherein the connecting part 7 of the vertical movement at the same time represents an arm of the parallelogram. The first and the second pair of articulated joints are mutually connected by means of the first arm 9a of the horizontal parallelogram and the second arm 9b of the horizontal parallelogram. One of the arms 9a and 9b of the horizontal parallelogram is provided with an opening for the lock element, which in case of releasing of the controller firmly connects the arm with the column, or alternatively, with the upper frame. In this exemplary embodiment, the lock element may be a pin with a mechanical spring. The lock element is coupled with a lever controller by means of a Bowden cable. Movement of the foot portion 2a is allowed after lowering from the upper vertical position, after pulling the controller, by means of which the lock element is controlled, and by simultaneous pushing or pulling of the foot portion 2a in the required direction. In the final position after releasing of the controller, the foot portion will be always automatically locked by means of the lock element.

Vertical movement of the foot portion in this exemplary embodiment is provided by means of a parallelogram, which comprises four articulated joints connection via arms, wherein the opposite arms of the parallelogram are of the same length. Movement of the foot portion is rotational. The surface of the foot portion 2a may be lifted up to the level of the rest area of the seating portion 3. Movement of the foot portion 2a is allowed after pulling the lever controller and simultaneously pulling or pushing the front edge of the foot portion 2a. First two articulated joints of the vertical movement mechanism are attached to the connection part 7 of the vertical movement on one side, wherein the connecting part 7 of the vertical movement at the same time represents an arm of the vertical parallelogram. The other two articulated joints are connected to the structure 12 of the foot portion, wherein the structure 12 of the foot portion at the same time represents an arm of the vertical parallelogram. The first and the second pair of articulated joints are mutually connected by means of the first arm 10a of the vertical parallelogram and the second arm 10b of the vertical parallelogram. The mechanism comprises also a lockable spring 13, which serves as a locking mechanism and prevents the portion from moving in case releasing the handle.

The lockable spring is rotationally attached to the connecting part 7 of the vertical movement on one side and it is rotationally attached to the foot portion 2a on the other side, or alternatively to the structure 12 of the foot portion.

Tilting of the foot portion 2a is performed by rotating it around the horizontal axis. The axis may be arranged in the center of the foot portion 2a or it may be arranged on the borders of the foot portion 2a. The horizontal axis is the rotational connection between the foot portion 2a and the structure 12 of the foot portion. Latching of the rotational movement is provided by means of lockable pneumatic spring 14 which keeps the foot portion 2a in the set position in case the spring is locked. The lockable pneumatic spring 14 is attached on one of its sides to the non-rotational part of the vertical movement mechanism of the foot portion and on its other side it is connected to the foot portion 2a, in the area distant from the rotation connection between the foot portion 2a and the structure 12 of the foot portion. Tilting of the foot portion 2a is allowed after pulling the controller, thus releasing the spring, and it is possible to manipulate with the foot portion 2a by pulling the edge of the portion in the required direction. In this embodiment, the controller is coupled by means of the Bowden cable with the lockable spring 14, which after releasing the controller prevents the foot portion from moving. The lockable spring 14 is locked in its default state.

Figure 6:
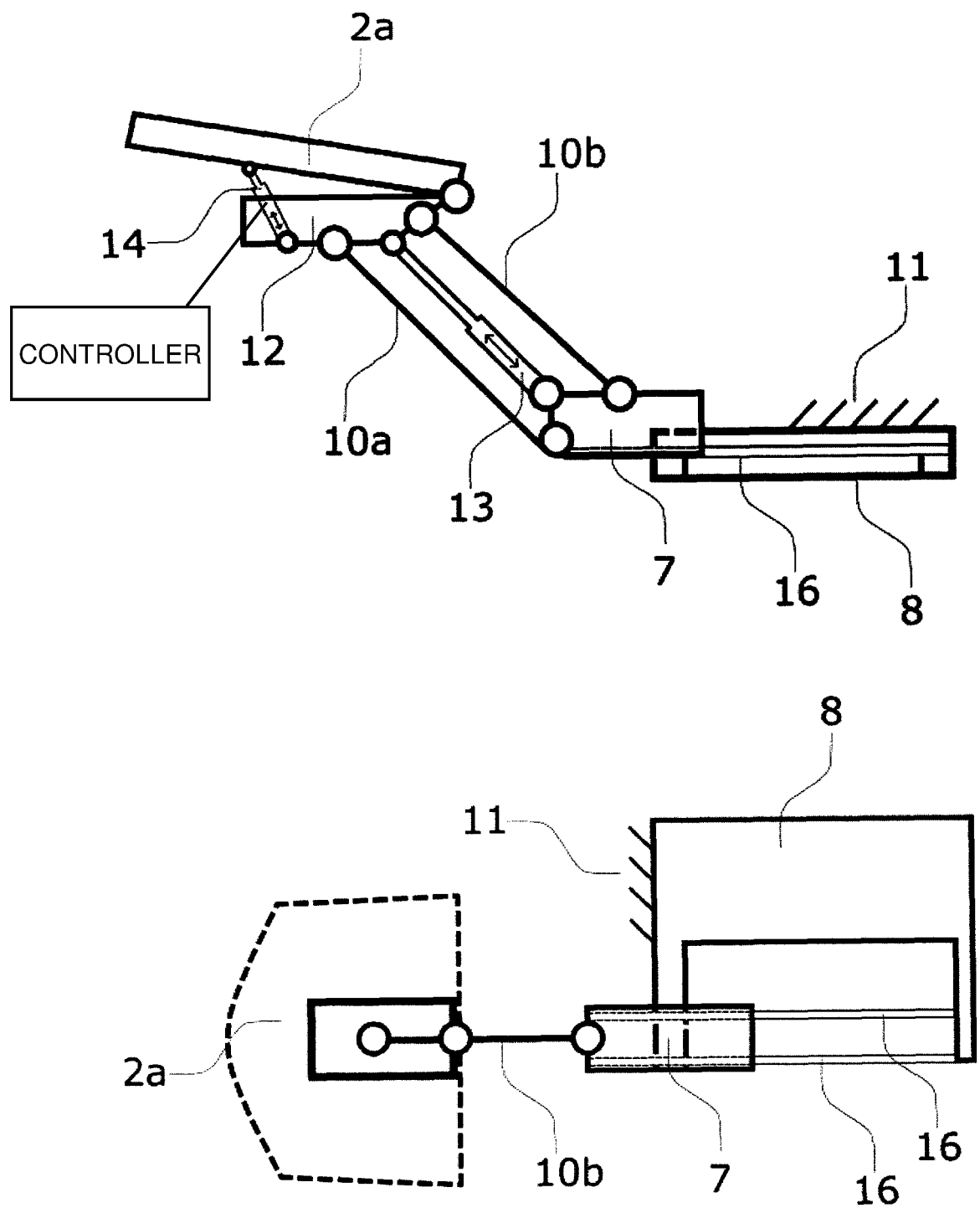
FIG. 6—schematic illustration of the structure of the positioning mechanisms of the foot portion with the parallelogram for vertical movement and with the linear guide for horizontal movement, and with the tilted rest area of the foot portion, in a side view and a top view.

The second exemplary embodiment is schematically illustrated in the FIG. 6. Movement of the foot portion 2a from the active to the inactive position under the rest area may be provided by means of one arm or a translational guide 16. Movement of the foot portion is translational or rotational or a combination thereof. Movement into the inactive position under the rest area in this exemplary embodiment is performed around the column 5, on which the horizontal movement mechanism is also attached, or by means of translational movement in the guide 16 attached to the rest area 1.

The horizontal movement mechanism between the active and the inactive position in this exemplary embodiment consists of one arm, which is on one of its side attached to the column 5 and on the other side it is attached to the connecting part 7, or it consists of the translational guide 16, which is attached to the rest area 1 and on its end it is attached to the connecting part 7 in order to firmly connect the horizontal and vertical movement mechanisms. Horizontal movement mechanism is provided with an opening for the lock element, which may be, in this exemplary embodiment, a pin with a mechanical spring. The lock element is coupled to the controller by means of a Bowden cable. Movement of the foot portion 2a is allowed after lowering from the upper vertical position after pulling the controller, by means of which the latching element is controlled, and simultaneous pushing or pulling the foot portion in the required direction. In the final position, upon releasing of the controller, the foot portion will be always locked by means of the lock element.

Vertical movement of the foot portion in this exemplary embodiment is provided by means of a parallelogram, which comprises four articulated joints connection via arms, wherein the opposite arms of the parallelogram are of the same length. Movement of the foot portion is rotational. It is possible to lift the surface of the foot portion 2a up to the level of the surface of the seating portion 3. Movement of the foot portion 2a is allowed after pulling the lever controller and simultaneously pulling or pushing the front edge of the foot portion 2a. First two articulated joints of the vertical movement mechanism are attached to the connection part 7 of the vertical movement on one side, wherein the connecting part 7 of the vertical movement at the same time represents an arm of the vertical parallelogram. The other two articulated joints are connected to the structure 12 of the foot portion, wherein the structure 12 of the foot portion at the same time represents an arm of the vertical parallelogram. The first and the second pair of articulated joints are mutually connected by means of the first arm 10a of the vertical parallelogram and the second arm 10b of the vertical parallelogram. The mechanism comprises also a lockable spring 13, which serves as a locking mechanism and prevents the portion from moving in case of releasing the handle. The lockable spring is rotationally attached to the connecting part 7 of the vertical movement on one side and it is rotationally attached to the foot portion 2a on the other side, or alternatively to the structure 12 of the foot portion.

Tilting of the foot portion 2a is performed by rotating it around the horizontal axis. The axis may be arranged in the center of the foot portion 2a or it may be arranged on the borders of the foot portion 2a. The horizontal axis is the rotational connection between the foot portion 2a and the structure 12 of the foot portion. Latching of the rotational movement is provided by means of lockable pneumatic spring 14 which keeps the foot portion 2a in the set position in case the spring is locked. The lockable pneumatic spring 14 is attached on one of its sides to the non-rotational part of the vertical movement mechanism of the foot portion and on its other side it is connected to the foot portion 2a, in the area distant from the rotation connection between the foot portion 2a and the structure 12 of the foot portion. Tilting of the foot portion 2a is allowed after pulling the controller, thus releasing the spring, and it is possible to manipulate with the foot portion 2a by pulling the edge of the portion in the required direction. In this embodiment, the controller is coupled with the lockable spring 14 by means of the Bowden cable, which after releasing the controller prevents the foot portion from moving. The lockable spring 14 is locked in its default state.

Figure 7:
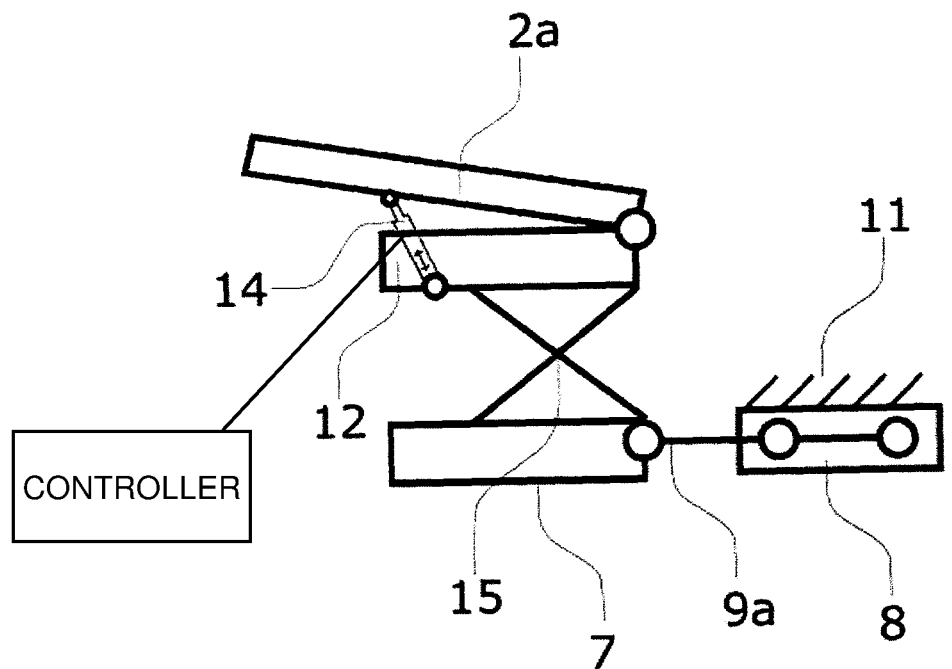
FIG. 7—schematic illustration of the structure of the positioning mechanisms of the foot portion for horizontal movement and with the scissor lift for vertical movement, and with the tilted rest area of the foot portion, in a side view and a top view.
Figure 7:
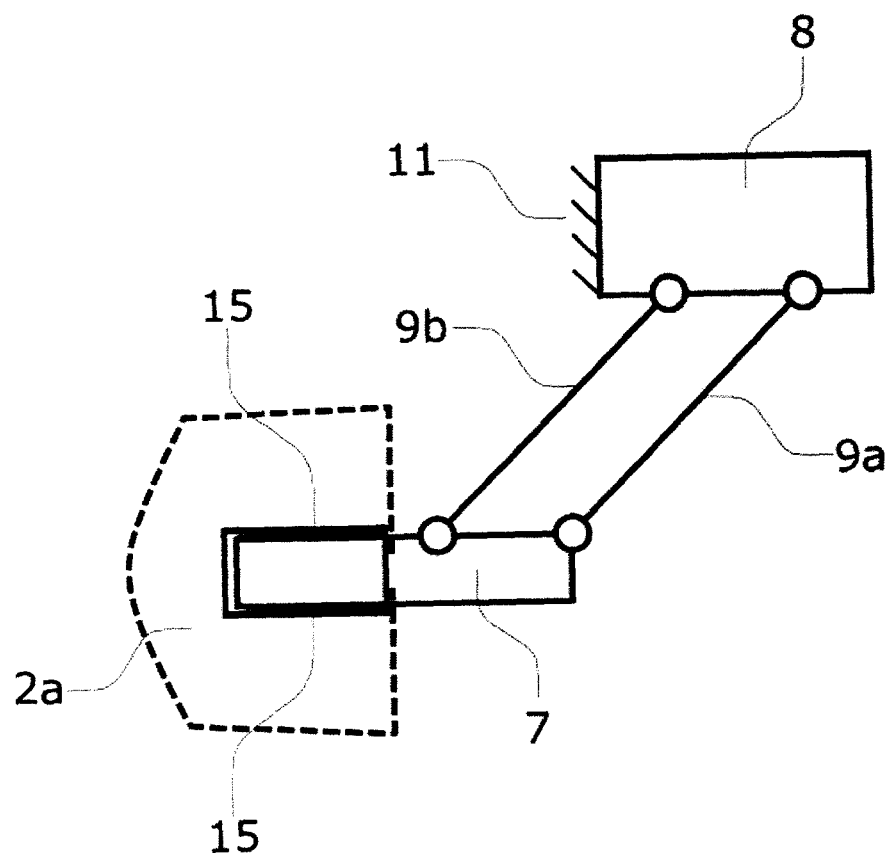

The third exemplary embodiment is schematically illustrated in the FIG. 7. Movement of the foot portion 2a from the active position to the inactive position under the rest area in this exemplary embodiment is provided by means of a parallelogram, which comprises four articulated joints connection via arms, wherein the opposite arms of the parallelogram are of the same length. Movement of the foot portion is rotational. Movement from the inactive position under the rest area in this exemplary embodiment is realized around the column 5, which is arranged under the side border of the rest area of the seating portion 3. The angle of movement of the mechanism is in the range of 0°-124° and in specific embodiments it depends on the position of the column 5 in structure of the medical bed. First two articulated joints of the parallelogram are attached to the fixed part 11 of the medical device, which is a column 5 or alternatively the upper frame or the connecting part 8 of the horizontal movement, wherein the fixed part 11 of the medical device at the same time represents an arm of the parallelogram. Other two articulated joints are attached to the connecting part 7 of the vertical movement, wherein the connecting part 7 of the vertical movement at the same time represents an arm of the parallelogram. The first and the second pair of articulated joints are mutually connected by means of the first arm 9a of the horizontal parallelogram and the second arm 9b of the horizontal parallelogram. One of the arms 9a and 9b of the horizontal parallelogram is provided with an opening for the lock element, which in case of releasing of the controller firmly connects the arm with the column, or alternatively, with the upper frame. In this exemplary embodiment, the lock element may be a pin with a mechanical spring. The lock element is coupled with a lever controller by means of a Bowden cable. Movement of the foot portion 2a is allowed after lowering from the upper vertical position, after pulling the controller by means of which the lock element is controlled, and by simultaneous pushing or pulling of the foot portion 2a in the required direction. In the final position after releasing the controller, the foot portion will be always automatically locked by means of the lock element.

Vertical movement of the foot portion in this exemplary embodiment is provided by means a scissor mechanism 15. Alternatively, it is possible to use other mechanisms, for example, a lever mechanism, or arranging the foot portion in the translational guide. Movement of the foot portion 2a may be translation or rotational, or a combination thereof. It is possible to lift the surface of the foot portion 2a up to the level of the rest area of the seating portion. The scissor mechanism 15 is on one of its sides attached to the horizontal movement mechanism of the foot portion and on the other side it is attached to the foot portion 2a, wherein the mechanism comprises also a lockable spring representing a lock element and preventing the portion from moving in case of releasing the controller. The lock element is connected with the controller by means of the Bowden cable. In the final position, upon releasing of the controller, the foot portion 2a will be always locked by means of the lock element.

Tilting of the foot portion 2a is performed by rotating it around the horizontal axis. The axis may be arranged in the center of the foot portion 2a or it may be arranged on the borders of the foot portion 2a. The horizontal axis is the rotational connection between the foot portion 2a and the structure 12 of the foot portion. Latching of the rotational movement is provided by means of lockable pneumatic spring 14 which keeps the foot portion 2a in the set position in case the spring is locked. The lockable pneumatic spring 14 is attached on one of its sides to the non-rotational part of the vertical movement mechanism of the foot portion and on its other side it is connected to the foot portion 2a, in the area distant from the rotation connection between the foot portion 2a and the structure 12 of the foot portion. Tilting of the foot portion 2a is allowed after pulling the controller, thus releasing the spring, and it is possible to manipulate with the foot portion 2a by pulling the edge of the portion in the required direction. In this embodiment, the controller is coupled with the lockable spring 14 by means of the Bowden cable, which so after releasing the controller prevents the foot portion from moving. The lockable spring 14 is locked in its default state.

LIST OF REFERENCE SIGNS

1—Rest area of the medical device
2—Foot segment
2a—Foot portion
2b—Foot supports
3—Seating portion
4—Back portion
5—Column
6—Chassis
7—Connecting part of the vertical movement
8—Connecting part of the horizontal movement
9a—First arm of the horizontal parallelogram
9b—Second arm of the horizontal parallelogram
10a—First arm of the vertical parallelogram 10b—Second arm of the vertical parallelogram
11—Fixed connection with the medical device
12—Structure of the foot portion
13—Lockable spring of the vertical movement
14—Lockable spring of the tilting
15—Scissor lift
16—Linear guide

The invention claimed is:

1. A medical device comprising:
a chassis,
a column supported in relation to the chassis,
a rest area supported in relation to the column configured to support a patient,
a foot portion configured to support feet of the patient, the foot portion being moveable by independent mechanisms, at least comprising:
a horizontal movement mechanism in the form of a horizontal parallelogram rotationally connected in relation to the rest area for moving the foot portion in a horizontal plane between an inactive position, around the column and under the rest area, to an active position, which is other than the inactive position, for supporting the feet of the patient, and
a vertical movement mechanism rotationally connected in relation to the horizontal movement mechanism for moving the foot portion in a vertical direction between a position substantially level with at least a portion of the rest area and a position below level with at least a portion of the rest area.

2. The device of claim 1, wherein the horizontal parallelogram comprises a first horizontal arm and a second horizontal arm connected in relation to the rest area by a first pair of articulated joints and connected in relation to the vertical movement mechanism by a second pair of articulated joints.

3. The device of claim 2, further comprising a latching element configured to release the arms for movement in relation to the rest area and firmly connect the arms in relation to the rest area.

4. The device of claim 3, wherein the latching element is controlled by a controller connected to the latching element by a Bowden cable.

5. The device of claim 1, wherein the vertical movement mechanism is in the form of a vertical parallelogram rotationally connected in relation to the horizontal parallelogram for moving the foot portion in the vertical direction.

6. The device of claim 5, wherein the vertical parallelogram comprises a first arm and a second arm connected in relation to the horizontal parallelogram by a first pair of articulated joints and connected in relation to the foot portion by a second pair of articulated joints.

7. The device of claim 6, further comprising a latching element configured to release the arms for movement in relation to the horizontal parallelogram and firmly connect the arms in relation to the horizontal parallelogram.

8. The device of claim 7, wherein the latching element is controlled by a controller connected to the latching element by a Bowden cable.

9. The device of claim 1, further comprising latching elements independently controlled to firmly connect the horizontal parallelogram in relation to the rest area and firmly connect the vertical movement mechanism in relation to the horizontal parallelogram, independently.

10. The device of claim 9, wherein the latching elements are controlled by controllers connected to the latching elements by Bowden cables.

11. The device of claim 1, wherein the vertical movement mechanism is in the form of a scissor mechanism connected in relation to the horizontal parallelogram for moving the foot portion in the vertical direction.

12. The device of claim 1, wherein the independent mechanisms further comprise a rotational connection between the foot portion and the vertical movement mechanism.

13. The device of claim 12, wherein the rotational connection provides rotation about a horizontal axis.

14. The device of claim 13, wherein the horizontal axis is arranged at a center of the foot portion.

15. The device of claim 13, wherein the horizontal axis is arranged at a border of the foot portion.

16. The device of claim 12, further comprising a latching element configured to release the foot portion for movement in relation to the vertical movement mechanism for adjusting the foot portion at an angle of tilt in relation to the vertical movement mechanism and firmly connect the foot portion in relation to the vertical movement mechanism to hold the foot portion at the angle of tilt in relation to the vertical movement mechanism.

17. The device of claim 16, wherein the latching element is controlled by a controller connected to the latching element by a Bowden cable.

18. The device of claim 12, further comprising latching elements independently controlled to firmly connect the horizontal parallelogram in relation to the rest area, the vertical movement mechanism in relation to the horizontal parallelogram, and the foot portion in relation to the vertical movement mechanism, independently.

19. The device of claim 18, wherein the latching elements are controlled by controllers connected to the latching elements by Bowden cables.

20. A medical device comprising:
a chassis,
a column supported in relation to the chassis,
a rest area supported in relation to the column configured to support a patient,
a foot portion configured to support feet of the patient, the foot portion being moveable by independent mechanisms, at least comprising:
a horizontal movement mechanism in the form of a horizontal parallelogram rotationally connected in relation to the rest area for moving the foot portion in a horizontal plane between an inactive position, around the column and under the rest area, to an active position, which is other than the inactive position, for supporting the feet of the patient,
a vertical movement mechanism in the form of a vertical parallelogram rotationally connected in relation to the horizontal movement mechanism for moving the foot portion in a vertical direction between a position substantially level with at least a portion of the rest area and a position below level with at least a portion of the rest area, and
a latching element configured to release the foot portion for movement in relation to the vertical movement mechanism for adjusting the foot portion at an angle of tilt in relation to the vertical movement mechanism and firmly connect the foot portion in relation to the vertical movement mechanism to hold the foot portion at the angle of tilt in relation to the vertical movement mechanism.

* * * * *